(12) United States Patent
Zhang et al.

(10) Patent No.: US 10,767,058 B1
(45) Date of Patent: Sep. 8, 2020

(54) CONTROLLED RELEASE MATERIALS FOR ANTI-CORROSION AGENTS

(71) Applicant: United States of America as Represented by the Administrator of the National Aeronautics and Space Administration, Washington, DC (US)

(72) Inventors: Xuejun Zhang, Orlando, FL (US); Wenyan Li, New Smyrna Beach, FL (US); Luz M. Calle, Merritt Island, FL (US)

(73) Assignee: United States of America as Represented by the Administrator of NASA, Washington, DC (US)

( * ) Notice: Subject to any disclaimer, the term of this patent is extended or adjusted under 35 U.S.C. 154(b) by 944 days.

(21) Appl. No.: 15/055,247

(22) Filed: Feb. 26, 2016

Related U.S. Application Data

(60) Provisional application No. 62/121,004, filed on Feb. 26, 2015.

(51) Int. Cl.
| | | |
|---|---|---|
| *C09K 15/32* | (2006.01) | |
| *C09D 5/08* | (2006.01) | |
| *C07C 211/63* | (2006.01) | |
| *C07D 277/72* | (2006.01) | |
| *C07D 233/58* | (2006.01) | |
| *C08B 37/16* | (2006.01) | |

(52) U.S. Cl.
CPC ............ *C09D 5/084* (2013.01); *C07C 211/63* (2013.01); *C07D 233/58* (2013.01); *C07D 277/72* (2013.01); *C08B 37/0012* (2013.01)

(58) Field of Classification Search
None
See application file for complete search history.

(56) References Cited

U.S. PATENT DOCUMENTS

| | | | |
|---|---|---|---|
| 6,319,108 B1 * | 11/2001 | Adefris | B24B 7/20 451/526 |
| 6,334,886 B1 * | 1/2002 | Barnes, Jr. | B01D 53/1425 210/662 |
| 7,790,225 B1 | 9/2010 | Calle et al. | |
| 9,227,221 B2 | 1/2016 | Calle et al. | |
| 2004/0255819 A1 * | 12/2004 | Sinko | C09D 5/086 106/14.42 |

(Continued)

OTHER PUBLICATIONS

M.F. Haase, et al., "Development of Nanoparticle Stabilized Polymer Nanocontainers with High Content of the Encapsulated Active Agent and Their Application in Water-Borne Anticorrosive Coatings," Adv. Mater. 2012, 24, 2429-2435.

(Continued)

*Primary Examiner* — Ronak C Patel
(74) *Attorney, Agent, or Firm* — Jonathan J. Leahy; Mark W. Homer

(57) ABSTRACT

Corrosion inhibitor materials are provided that release active corrosion inhibitor compounds when they are most needed—in response to changes in conditions, including acid or basic pH, that cause corrosion or occur at the early stages of corrosion. The materials comprise particles that can be dispersed in paints and coatings for metals. The particles in some cases include ionic water-soluble anti-corrosion agents complexed to oppositely charged surfactants and entrapped in silica oxide or metal oxide gels.

11 Claims, 6 Drawing Sheets

(56) References Cited

U.S. PATENT DOCUMENTS

2011/0048275 A1* 3/2011 Fletcher .................. C09C 3/08
106/14.05
2011/0053275 A1* 3/2011 Lalgudi ................. C09D 5/086
436/6

OTHER PUBLICATIONS

Y. Wu, et al., "Monodispersed or narrow-dispersed melamine-formaldehyde resin polymer colloidal spheres: preparation, size-control, modification, bioconjugation and particle formation mechanism," J. Mater. Chem. B, 2013, 1, 204-212.

G. Wu, et al., "A Versatile Approach towards Multifunctional Robust Microcapsules with Tunable, Restorable, and Solvent-Proof Superhydrophobicity for Self-Healing and Self-Cleaning Coatings," Adv. Funct. Mater. 2014, 24, 6751-6761.

A.N. Khramov, et al., "Sol-gel-derived corrosion-protective coatings with controllable release of incorporated organic aorrosion inhibitors," Thin Solid Films, 2005, 483, 191-196.

D. Borisova, et al., "Mesoporous Silica Nanoparticles for Active Corrosion Protection," ACS. NANO. 2011, 5, 3, 1939-1946.

A. Chenan, et al., "Hollow mesoporous zirconia nanocontainers for storing and controlled releasing of corrosion inhibitors," Ceramics International, 2014, 40, 10457-10463.

N. Selvakumar, et al., "Smart coating for corrosion protection by adopting nano particles," Process in Organic Coatings, 2012, 74, 461-469.

N. Wang, et al., "Preparation and characterization of epoxy composites filled with functionalized nano-sized MCM-41 particles", J. Mater. Sci. 2008, 43, 3683-3688.

S. Zheng, et al., "Inorganic-organic sol gel hybrid coatings for corrosion protection of metals," J. Sol-Gel. Sci. Technol. 2010, 54, 174-187.

A.N. Khramov, et al., "Hybrid organo-ceramic corrosion protection coatings with encapsulated organic corrosion inhibitors," Thin Solid Films, 2004, 447-448, 549-557.

* cited by examiner

CONTROLLED RELEASE MATERIALS FOR ANTI-CORROSION AGENTS

CROSS REFERENCE TO RELATED APPLICATIONS

This application claims the benefit of priority under 35 U.S.C. § 119(e) from U.S. Provisional Patent Application Ser. No. 62/121,004 filed on Feb. 26, 2015, the contents of which are incorporated herein by reference.

ORIGIN OF THE INVENTION

The invention described herein was made in the performance of work under a NASA contract and by an employee of the United States Government and is subject to the provisions of Section 20135(b) of the National Aeronautics and Space Act, Public Law 111-314, § 3 (124 Stat. 3330, 51 U.S.C. Chapter 201), and may be manufactured and used by or for the Government for governmental purposes without the payment of any royalties thereon or therefore.

FIELD OF DISCLOSURE

The present invention relates generally to materials that give controlled release of corrosion inhibitors.

BACKGROUND OF THE INVENTION

Organic coatings offer the most common and cost-effective protection for metallic structures against degradation in corrosive environments. However, the metal substrate loses this passive protection when disruption of the coating occurs. Recently, active corrosion protection coatings, commonly referred to as "smart coating, intelligent coating, functional coating, or self-healing coating," have become an attractive research topic. A smart coating is a coating with incorporated "smart" micro/nanostructured containers or carriers. These containers filled with corrosion inhibitors not only preferably preclude the direct contact between the active anticorrosive agent and the adjacent environment (such as paint resins), but, intelligently release the host active agent at a corrosion site over a period of time. Such a coating with dispersed "smart containers" can provide long-term effective corrosion protection for metallic substrates. For example, U.S. Pat. No. 7,790,225 discloses a coating with pH-sensitive microcapsules that contain and release anticorrosive agents. A change of pH induced by the metallic corrosion process can be used as a trigger to break down or disintegrate the shells chemically to release the active compounds on-site.

Many organic and inorganic anticorrosive compounds can be encapsulated in polymeric carriers, but some highly reactive and very water-soluble agents (mostly ionic compounds) are difficult to incorporate in organic matrices. Polymeric microcapsules, prepared by water-in-oil microemulsion polymerization, for example U.S. Pat. No. 9,227,221, were designed for encapsulation of water-soluble inorganic corrosion inhibitors. However, some water-soluble corrosion inhibitors cannot be encapsulated by these polymer capsules due to the reactivity of the inhibitors in the presence of the carrier materials.

New controlled-release anticorrosion materials are needed, particularly for controlled-release of water-soluble anticorrosion agents.

SUMMARY OF THE INVENTION

An objective of the present invention is to provide an inorganic, organic, or organic/inorganic hybrid controlled-release system and a novel preparation method to effectively encapsulate active agents such as organic and inorganic anticorrosive agents, especially water-soluble corrosion protection agents.

More specifically, an objective of the present invention is to provide inorganic, organic, or organic/inorganic hybrid controlled-release materials as carriers of water-soluble anticorrosive inhibitors. Most of the controlled-release materials for water-soluble anticorrosive inhibitors in the present invention are based on silica and/or metal oxides. The inorganic carrier matrix entrapping the anticorrosion agent can be partially and gradually dissolved or broken down under either strong basic or acidic conditions, depending on the matrix structure (silica or metal oxide, and which particular metal oxide), to provide pH-controlled release as well as time-release of the active ingredient. In other embodiments of the invention, the carrier releases the active agent upon heating.

One embodiment provides a corrosion inhibitor material comprising: particles comprising: (I) a complex comprising: (a) an ionic surfactant, an ionic polymer, an ionic polymer precursor, or an ionic liquid; and (b) an ionic water-soluble corrosion inhibitor; wherein (a) and (b) have opposite charges; wherein the particles have (i) the property that if they are placed in an aqueous solution in an acidic pH they release some of the water-soluble corrosion inhibitor, (ii) the property that if they are placed in an aqueous solution in a basic pH they release some of the water-soluble corrosion inhibitor, or (iii) the property that if they are heated they release some of the water-soluble corrosion inhibitor. The particles typically further comprise (II) a solid or gel matrix structure entrapping complex (I).

Another embodiment provides a method of forming a corrosion inhibitor material comprising: (1) dissolving in a polar solvent solution (typically an aqueous solution) (a) an ionic surfactant, an ionic polymer, an ionic polymer precursor, or an ionic liquid; and (b) an ionic water-soluble corrosion inhibitor; wherein (a) and (b) have opposite charges; (2) forming a complex of (a) with (b); and (3) forming particles comprising the complex of (a) with (b); wherein the particles have (i) the property that if they are placed in an aqueous solution in an acidic pH they release some of the water-soluble corrosion inhibitor, (ii) the property that if they are placed in an aqueous solution in a basic pH they release some of the water-soluble corrosion inhibitor, or (iii) the property that if they are heated they release some of the water-soluble corrosion inhibitor. Typically the method comprises dissolving in the polar solvent solution a matrix-forming molecule that in an aqueous solution can form a gel or polymer that can break down or molecularly rearrange at an acidic or a basic pH in an aqueous solution and is relatively more stable at a more neutral pH; wherein the method forms particles comprising a solid or gel matrix formed from the matrix-forming molecule, the particles comprising the complex of (a) with (b).

Another embodiment provides a method of forming a corrosion inhibitor material comprising: (1) dissolving in an aqueous solution (a) a cyclodextrin; and (b) a water-soluble corrosion inhibitor; (2) forming a complex of (a) with (b); (3) dissolving in the aqueous solution a matrix-forming molecule that in an aqueous solution can form a gel or polymer that can break down or molecularly rearrange at an acidic or a basic pH in an aqueous solution and is relatively more stable at a more neutral pH; and (4) forming particles comprising a solid or gel matrix formed from the matrix-forming molecule, the particles comprising the complex of (a) with (b); wherein the particles have (i) the property that if they are placed in an aqueous solution in an acidic pH they release some of the water-soluble corrosion inhibitor, (ii) the property that if they are placed in an aqueous solution in a basic pH they release some of the water-soluble corrosion inhibitor, or (iii) the property that if they are heated they release some of the water-soluble corrosion inhibitor.

The present invention of controlled-release particles can be effectively dispersed into various coatings including polymer-based coatings, waterborne coatings, sol-gel coatings, or hybrid coatings, which can then be coated onto metals susceptible to corrosion. The microstructures and properties of these particles can be designed to optimize controlled release characteristics for corrosion protection.

DETAILED DESCRIPTION OF THE INVENTION

Hereinafter, the contents of the present invention will be described in detail. The foregoing description is illustrative only and is not intended to be in any way limiting. In addition to the illustrative aspects, embodiments, and features described above, further aspects, embodiments, and features will become apparent by reference to the drawings and the following detailed description.

A principal feature of the present invention is to encapsulate one or more water-soluble corrosion inhibitor compound(s) into inorganic carriers to achieve controlled release under basic or acidic conditions. In accordance with the present invention, the solubility and mobility of water-soluble corrosion inhibitor compounds, such as sodium molybdate, are reduced by complexing with an oppositely charged compound, most often cationic surfactant cetyltrimethyl-ammonium halide in an aqueous solution. The surfactant-immobilized water-soluble inhibitors may self-assemble into a micelle. In general a matrix-forming molecule is then added, and then undergoes a sol-gel reaction to form a gel matrix around the micelles. In the examples, the matrix-forming molecule is typically tetraethylortho silicate (TEOS) ($Si(OC_2H_5)_4$), also known as tetraethoxysilane. With only a modest increase of pH by the addition of ammonium hydroxide (to a pH about 9), the TEOS undergoes hydrolysis and condensation to form branched and linear silica polymers:

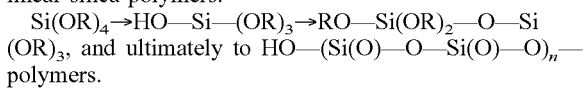

$Si(OR)_4 \rightarrow HO—Si—(OR)_3 \rightarrow RO—Si(OR)_2—O—Si(OR)_3$, and ultimately to $HO—(Si(O)—O—Si(O)—O)_n$—polymers.

Figure 1:
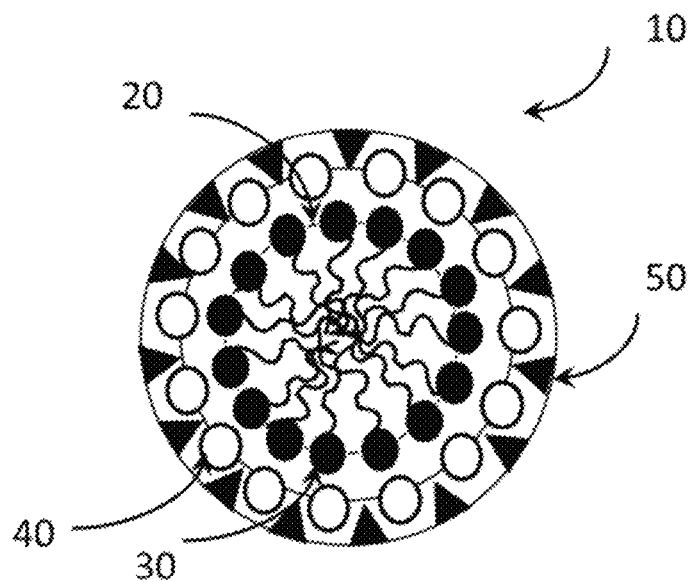
FIG. 1 illustrates an embodiment of a meso-structured building block.

This silica matrix or cage then encases and protects the surfactant-corrosion inhibitor ionic complex. This produces micro-structured or meso-structured building blocks 10 shown in FIG. 1.

The micro-/meso-structured building block 10 initiated from a micelle 20. Within the micelle, there are some number of supporting molecules 30, such as a surfactant and the like, and anticorrosive compounds 40, such as a water soluble corrosion inhibitive compound. Around the micelle, there are carrier materials 50 co-assembled, such as silica or other metal oxides. It is noted that the lines between the solid shapes are a representational depiction of the spherical micelle and the similar shape of molecular aggregation around it. The ordered or disordered aggregation of a number of micro-/meso-structured building blocks forms a micro-/meso-structured controlled-release particle or material. In some cases, one micelle may be found in a particle. But more typically, several micelles are encased in a more continuous supporting matrix of silica, or the like, to form a particle. The particles typically have a size of 0.05 to about 50 microns in diameter.

The initiation of metal corrosion can raise local pH at or near a metal surface, and this partially hydrolyzes the silica matrix of the particle to release the surfactant-corrosion inhibitor complex and the free corrosion inhibitor. The rise in pH also typically breaks down the ionic bonds holding the surfactant-corrosion inhibitor ionic complex together, and this also contributes to release of the corrosion inhibitor.

In other embodiments, there is no matrix. The ionic complex with the ionic surfactant (or ionic polymer or ionic polymer precursor) complexed to the oppositely charged ionic corrosion inhibitor may precipitate into particles. These particles alone, without a silica matrix or other type of matrix, can be controlled-release particles and can constitute the controlled-release material. An example of this is Example 3 below.

One embodiment presented herein provides a method of forming a corrosion inhibitor material comprising: (1) dissolving in an aqueous solution (a) an ionic surfactant, an ionic polymer, an ionic polymer precursor, or an ionic liquid; and (b) an ionic water-soluble corrosion inhibitor; wherein (a) and (b) have opposite charges; (2) forming a complex of (a) with (b); and (3) forming particles comprising the complex of (a) with (b); wherein the particles have (i) the property that if they are placed in an aqueous solution in an acidic pH they release some of the water-soluble corrosion inhibitor, (ii) the property that if they are placed in an aqueous solution in a basic pH they release some of the water-soluble corrosion inhibitor, or (iii) the property that if they are heated they release some of the water-soluble corrosion inhibitor. In specific embodiments, the basic pH where the particles release some of the corrosion inhibitor is pH 12 or above, or pH 13 or above. In specific embodiments, the acidic pH where the particles release some of the corrosion inhibitor is pH 2 or below or pH 1 or below. In specific embodiments where the particles release some of the corrosion inhibitor with heating, they have the property that they release some of the corrosion inhibitor at a temperature of above 70° C., above 100° C., above 200° C., or above 300° C.

The term "ionic liquid" as used herein refers to a salt that in pure form is a liquid at temperatures below 100° C. When reference is made to the charge of an ionic liquid herein, this means the charge of the larger molecular weight ion of the two ions in the ionic liquid. For instance, 1-alkyl-3-methylimidazolium chloride (AMC) is an ionic liquid used in Example 6 below. Chloride is merely a counter ion in this. The charge of the ionic liquid, in this example as used herein, refers to the charge of the larger molecular weight ion, in this case 1-alkyl-3-methylimidazolium.

The preferred ionic surfactants are cationic because most of the suitable corrosion inhibitors are anionic. A preferred cationic surfactant is hexadecyltrimethylammonium bromide, also known as cetyltrimethylammonium bromide. More generally, the surfactant can be alkyl ($C_8$-$C_{22}$) trimethylammonium X (where X refers to a selected halogen anion, such as chloride, bromide, fluoride, and iodide), for instance, cetyltrimethylammonium X, dodecyltrimethylammonium X, tetradecyltrimethylammonium X, hexadecyltrimethylammonium X, octadecyltrimethylammonium X, or dodecyltrimethylammonium X. Or it can be alkylammonium methosulfate, alkyldimethylammonium methosulfate, cetyltrimethylammonium hydrogensulfate, hexadecyltrimethylammonium p-toluenesulfonate, or cetylpyridinium chloride. It may also be bis(cetyldimethylammonium)butane dibromide ($C_{16}C_4C_{16}Br_2$), or a similar bis-structured surfactant.

Some corrosion inhibitors are cationic, including some metal salts. For these, anionic surfactants or other anionic complex partners are useful. Anionic surfactants that can be used in some embodiments of the invention include alkyl ($C_8$-$C_{22}$) sulfate Y, where Y is a cation such as sodium. Examples are sodium dodecylsulfate and sodium hexadecylsulfate. $C_8$-$C_{22}$ fatty acids can also be used as anionic surfactants.

Preferably the cationic and anionic surfactants have $C_{12}$-$C_{22}$ alkyl chains. Ionic liquids can also be used to complex the ionic corrosion inhibitor. Preferred ionic liquids are alkyl-substituted imidazolium and pyridinium cations, with halide counterions. An example is 1-alkyl-3-methylimidazolium chloride (AMC) in Example 6 below. Other examples are 1-alkylpyridinium and N-methyl-N-alkylpyrrolidinium.

A cationic monomer precursor to a polymer would be 3-(methacryloylamino) propyl trimethylammonium chloride (MPTA) (Example 8 below) or acrylamido-N-propyltrimethylammonium chloride (APTA).

Anionic polymer precursors include methacrylic acid (MA) and 2-acrylamido-2-methyl-1-propane sulfonic acid (APSA).

Cationic polymers useful as the ionic partner to the corrosion inhibitor in the complex can be poly-MPTA, poly-APTA, poly-MPTA-APTA copolymers, polylysine, diethylamino-cellulose, triethylamino-cellulose, or other suitable polymers.

Anionic polymers can be polymethacrylic acid, poly-APSA, polyglutamic acid, sulfoethyl-cellulose, carboxymethyl-cellulose, or other suitable polymers.

The ionic water-soluble corrosion inhibitor may be any ionic water-soluble corrosion inhibitor. Suitable compounds include the following acids and their salts:

ortho-phosphoric, pyrophosphoric, tripoly-phosphoric, polyphosphoric acid;

mono- and di-alkyl or aryl-esters of ortho-phosphoric and pyro-phosphoric acid;

metaphosphoric, trimeta-phosphoric, poly-metaphosphoric acid;

phosphorous (phosphonic) acid and derivatives of phosphonic acid, such as compounds known in industrial practice as NMPA and HEDPA;

alkyl and aryl esters of thio-phosphoric and dithio-phosphoric acid;

molybdic, phospho-molybdic, silico-molybdic acid;

boric acid;

cyanamidic acid;

nitrous acid;

derivatives of thio- and dithiocarbonic acid, such as o-alkyl esters;

derivatives of dithiocarbamic acid, such as N-alkyl dithiocarbamates;

pyrrolidinecarbodithioic acid;

various thio-organic compounds functionalized with one or multiple —SH group of acidic character, including: 2,5-dimercapto-1,3,4-thiadiazole or Bismuthiol I, and 2,4-dimercapto-s-triazolo-[4,3-b]-1,3-4-thiadiazole or $C_3H_2N_4S_3$, and 1,3,5-triazine-2,4,6(1H,3H,5H)-trithione, or trithiocyanuric acid (TMT), and dithiocyanuric acid;

various N,N-, S,S- and N,S-substituted derivatives of the above compounds, such as 5-mercapto-3-phenyl-1,3,4-thiadiazoline-2-thione or Bismuthiol II and 5,5' thio-bis(1,3,4 thiadiazole-2(3H)-thione;

various S-substituted derivatives of trithiocyanuric acid;

dimer and polymer derivatives of the above, resulting from oxidative dimerization or polymerization of di- and poly-mercapto compounds, such as: 5,5' dithio-bis (1,3,4 thiadiazole-2(3H)-thione or (DMTD)2, and (DMTD)n, the polymer of DMTD and (TMT)2, the dimer and polymers of TMT;

soluble salts of DMTD and TMT; poly-ammonium salt of DMTD or (DMTD)n and TMT formed with polyamines;

selected mercapto derivatives: mercapto-benzothiazole, mercapto-benzoxazole, mercapto-benzimidazole, or combinations of the above;

di- or poly-mercapto organic compounds such as: di-mercapto derivatives of thiophene, pyrrole, furane, and of diazoles and thiadiazoles;

di- and tri-mercapto derivatives of pyridine, diazines, triazines and of benzimidazole and benzothiazole, such as: dimercaptopyridine, 2,4-dithiohydantoine, and 2,4-dimercapto-6-amino-5-triazine; and carboxylic and di-carboxylic acids such as: ascorbic, salicylic acid, phthalic acid, nitro-phthalic acid and succinic acid; and derivatives of succinic acid such as: 1-(benzothiazol-2-ylthio)succinic acid.

Other suitable compounds include the compounds containing the following cationic species: Li, Mg, Al, Zn, Ca, Sr, La, Ce, Fe, and Bi; such as their oxides, hydroxides, and various salts.

Some preferred examples of water-soluble corrosion inhibitors include: sodium molybdate, lithium molybdate, potassium nitrite, calcium nitrite, alkali metal nitrite, cerium (III) nitrate, carbonates, sodium phosphate, calcium metaborate, and sodium metasilicate, lithium metasilicate, potassium metasilicate, sodium orthovanadate, sodium orthotungstate, ammonium orthotungstate, sodium chromate, potassium chromate, sodium 2-mercaptobenzothiazole, potassium 2-mercaptobenzothiazole, ammonium 2-mercaptobenzothiazole, ammonium benzoate, or mixture thereof.

Figure 8:
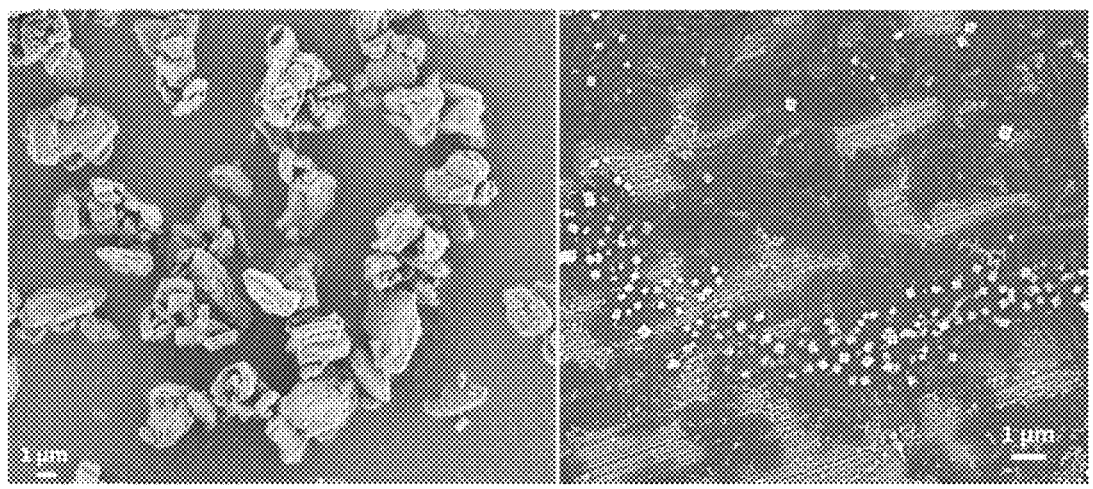
FIG. 8 shows SEM micrographs of the particles of NaMBT-$C_n$TA from Example 3 before heating (image on left side) and after heating (image on right side).

In some embodiments of the invention, forming the controlled-release material comprises a formation of an initial complex and a matrix. For example, the initial complex comprises the reaction product of sodium molybdate or sodium or potassium salts of 2-Mercaptobenzothiazole and a counter ionic surfactant such as alkyltrimethylammonium halide ($C_nTAX$, where X refers to a selected halogen anion, such as chloride, bromide, fluoride, and iodide and n refers to the number of carbon atoms). This complex could be solid like an aggregation (such as flocculate, precipitate, or colloid) or water soluble. In the case of molybdate and $C_{16}TAX$, the complex formed is water soluble; while in the case of sodium 2-mercaptobenzothiazole and $C_{16}TAX$, the initial complex is solid (as shown in FIG. 8). The formation of the initial complex is advantageous in that the very water soluble sodium molybdate can be immobilized by $C_nTAX$ and subsequently self-assembled into micro-/meso-structured micelles around which inorganic precursor sol-gel reactions occur to form a matrix (for instance, a silica matrix) around the ionic complex micelles or ionic complex particles. This forms a micro-structured or meso-structured inorganic framework.

The ionic complex itself dissociates in acid or alkaline conditions, at the same time that the silica matrix hydrolyzes in acid or alkaline conditions. So these two mechanisms work together to provide controlled release of the corrosion inhibitor with acid or alkaline pH.

Some ionic complex particles are thermally sensitive as well, such as NaMBT-$C_nTA$ complex (refers to sodium 2-mercaptobenzothiazole-cetyltrimethylammonium), which provides both pH and temperature as a dual stimuli-responsive controlled release function. In this case, above a certain temperature, or above or below a certain pH value, the bound active compound is mobilized.

Figure 2:
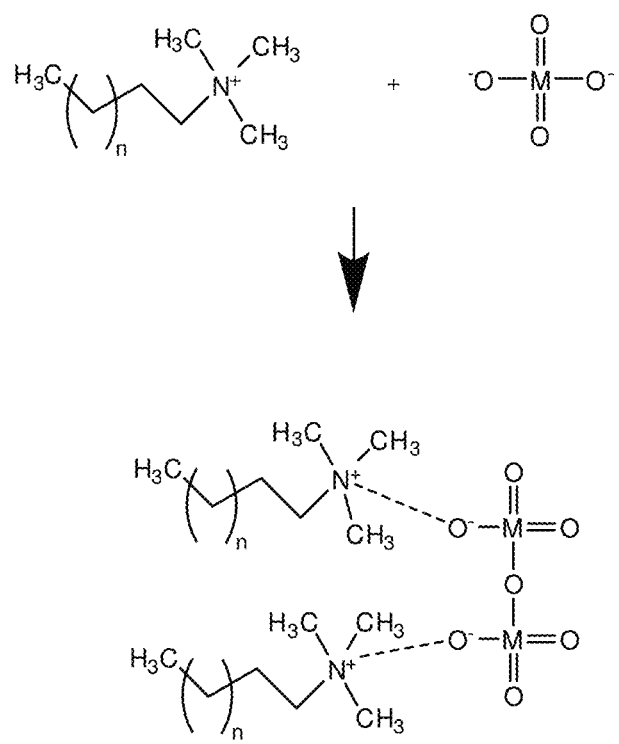
FIG. 2 presents a formation of initial complex M-CnTA.

In some embodiments of the invention, the general formation of the initial complex between molybdate-type salts and $C_nTAX$ type surfactants is presented in FIG. 2.

In detail, as shown in FIG. 2, with the multivalent metal (M) anion, which is preferably one or more of the anions $MoO_4^{2-}$, $Cr_2O_7^{2-}$, $WO_4^{2-}$, $VO_4^{3-}$, $SiO_3^{2-}$, linking two alkyltrimethylammonium chains, the complexes are of the type M-cetryltrimethyl-ammonium (M-$C_nTA$) form (where M refers to metal atom in the ionic group). FIG. 2 shows two metal ions bridged to each other, and thereby linking to two surfactant chains. In the case of some other organic anions such as ionic mercaptobenzothiazole, the anions may link to just one alkyltrimethylammonium chain.

In some embodiments, the present invention also relates to an encapsulation by a matrix. The matrix can be or can include $SiO_2$. In some embodiments, the matrix is or includes materials such as $SiO_2$, $TiO_2$, $Al_2O_3$, $CaO$, $ZnO_2$, $MgO$, $ZrO_2$, $V_2O_3$, $V_2O_5$, $Cu_2O$, $CuO$, $Mn_2O_3$, $Mo_2O_3$, $WO_3$, $Fe_3O_4$, or combinations thereof. In some embodiments, it is carbon. In the case of a $SiO_2$ carrier, the precursors include tetraethyl orthosilicate (TEOS), sodium metasilicate, tetramethyl orthosilicate (TMOS), and other $SiO_2$ resources. Oxides of silicon, aluminum, zirconium, calcium, titanium, vanadium, and some other transition metal oxides can be dissolved in either a strong basic or acidic solution, depending on the oxide. For example, solid silica particles can be partially dissolved where the pH is basic from about 10 to 13.5, more preferably from about 12 to about 13.5. Also, solid alumina can be dissolved under both acidic and basic conditions—where the pH is lower than 3 or higher than 10.5. Rather than resorting to organic functional groups, the inorganic carriers (matrix) can be partially or totally broken down under acidic or basic conditions so as to endow the devices with functionality of the release in the control of pH change in their microenvironment resulting from the corrosive process. In some embodiments, the matrix is or includes Si and/or metal materials such as Al, Fe, Mg, Mn, Cu, Zn, Ca, Ti, Sn, Mo, W, Co, Pd, Pt, Zr, Ni, or combinations thereof. But, it is not limited thereto.

In other embodiments, cyclodextrin may complex the corrosion inhibitor. Cyclodextrin is a doughnut-shaped molecule that can partition certain ionic complexes as described herein in the center of the doughnut. The cyclodextrin-inhibitor complex can then be encased in a silica matrix or other matrix as described herein. The cyclodextrin may bind the water-soluble corrosion inhibitor by hydrogen bonds or by hydrophobic interactions.

In some embodiments, the controlled-release particles are spherical. In some embodiments, the particles are more irregularly shaped. The internal structure of the particles or material, like the shape of the particles, may be random and/or asymmetric, regular or irregular. But the size of the particles should be in the general range of several micrometers or submicrons so that the particles are small enough to be embedded into a standard coating layer.

In some embodiments, the reaction to create the controlled-release materials is carried out by dissolving the water-soluble corrosion inhibitor, such as potassium nitrite, and the supporting molecule (ionic partner to the corrosion inhibitor), such as alkyltrimethylammonium surfactants $C_nTAX$, in a suitable aqueous solvent, such as, for example, distilled water to dissolve the inhibitor and $C_nTAX$. In some embodiments, the reaction is carried out by dispersing the corrosion inhibitor, such as 2-mercaptobenzothiazole (MBT), into the supporting molecule aqueous solution. Sodium MBT is highly soluble in water, but the acid form of MBT must be ionized by raising the pH to fully dissolve, for instance by ammonium hydroxide addition. The aqueous solution is then combined with silicon oxide or metal oxide precursors such as TEOS in an approximate stoichiometric ratio to produce a white floccule, which is solid, for example, N—$C_nTA$-Si (refers to nitrite-alkyltrimethylammonium-silica) or MBT-$C_nTA$-Si (refers to mercaptobenzothiazole-alkyltrimethylammonium-silica). After a sol-gel condensation reaction and aging process, the controlled-release material can be isolated. The controlled release particulate material, such as N—$C_nTA$-Si or MBT-$C_nTA$-Si, can be separated from the bulk aqueous solution by a suitable means, such as spray drying, and used as a corrosion inhibitor carrier as well as a pigment for addition to paints and sealants.

In some embodiments, either the ionic carrier that complexes with the anti-corrosion agent or the matrix can adsorb negatively charged ions from the environment specifically, aggressive corrosive ions such as chloride. The cationic surfactant or other cationic ionic carrier is oppositely charged to chloride and can bind it. Local partial positive charges on the matrix, such as from Si or metal atoms in silica or metal oxides, can also attract and bind chloride.

Some embodiments of the methods for preparing controlled release materials may further include an additional step of introducing a polymer that breaks down in ultraviolet light, thus releasing the inhibitor in prolonged exposure to sunlight.

An example of this approach is introducing polystyrene into a silica framework, as in Example 11 below. With polystyrene, the encased inhibitors can be released when the materials are exposed to prolonged sunlight or UV light, because polystyrene and its copolymers can be degraded with ultraviolet light. The polystyrene incorporation also substantially modifies the thermal and rheological properties of the silica.

The controlled-release material, for instance Mo-$C_n$TA-Si, N—$C_n$TA-Si, NaMBT-$C_n$TA-Si or MBT-$C_n$TA-Si particulate material, is typically removed from the aqueous solution in which it was created by one of several processes: filtration, centrifugation, spray drying, heat drying, air drying, vacuum drying, or a combination of more than one of these. It may also be washed with water or another solvent before fully drying it. It also will not always need to be fully dried.

The particles are then added to a film-forming composition to form a film-forming suspension. The film-forming composition can be waterborne or solvent-based organic coatings or inorganic coatings. Examples of solvent-based coatings include solvent-based polymer coatings containing alkyd, epoxy, epoxy ester, polyester melamine, polyurethane, polyvinyl butyral, and thermoplastic acrylics resins. Examples of waterborne coatings include water soluble polyesters, polyacrylates, alkyds, epoxies and epoxy esters; water-dispersible vinyl propionate copolymers, vinyl acetate copolymers, acrylate-methacrylate copolymers, and styrene-butadiene copolymers and polymers; styrene-butadiene copolymers, acrylics, alkyds, polyvinyl acetate, and polystyrene latex; and water-based alkyds and polyurethane. Examples of inorganic coatings include silicon-based inorganic coatings, and other sol-gel coatings and pretreatments. The coating can also be a latex coating. Typically the controlled-release particle concentration is about 1 to 5% by weight or about 1 to 10% by weight.

One embodiment of the invention provides a method of forming a corrosion inhibitor material comprising: (1) dissolving in polar solvent solution (typically an aqueous solution) (a) an ionic surfactant, an ionic polymer, an ionic polymer precursor, or an ionic liquid; and (b) an ionic water-soluble corrosion inhibitor; wherein (a) and (b) have opposite charges; (2) forming a complex of (a) with (b); and (3) forming particles comprising the complex of (a) with (b); wherein the particles have (i) the property that if they are placed in an aqueous solution in an acid pH they release some of the water-soluble corrosion inhibitor, (ii) the property that if they are placed in an aqueous solution in a basic pH they release some of the water-soluble corrosion inhibitor, or (iii) the property that if they are heated they release some of the water-soluble corrosion inhibitor. Typically the method comprises dissolving in the polar solvent solution a matrix-forming molecule that in an aqueous solution can form a gel or polymer that can break down or molecularly rearrange at an acidic or a basic pH in aqueous solution and is relatively more stable at a more neutral pH; wherein the method forms particles comprising a solid or gel matrix formed from the matrix-forming molecule, the particles comprising the complex of (a) with (b).

Silica gels and metal oxide gels have the property that they break down or molecularly rearrange at acidic and basic pHs and are more stable at a more neutral pH. The more neutral pH is not necessarily pH 7, although these gel matrices are generally stable at pH 7. Silica gels in the Examples below are generally formed at pH 10, and they are most stable at the pH at which they are formed. At a more elevated pH, such as pH 12 or 13, the silica gels hydrolyze some bonds. Different bonds are typically reformed, which constitutes the molecular rearrangement. In this process of matrix break down and/or molecular rearrangement, the corrosion inhibitor trapped in the particles is at least partially released. At acidic pHs, silica and metal oxide gels also hydrolyze and/or molecularly rearrange. Silica gel particles of the invention at acidic pHs typically form smaller particles as the gel bonds rearrange, and this expels some of the corrosion inhibitor.

In a more specific embodiment the matrix-forming molecule is an oxide or alkoxide of silicon or of a metal.

In one embodiment the complex of (a) with (b) precipitates to form the particles.

In some embodiments (a) is cationic and (b) is anionic. In other embodiments, (a) is anionic and (b) is cationic.

In some embodiments (a) is a cationic surfactant.

In some embodiments, (b) is nitrite, molybdate, or 2-mercaptobenzothiazole. In these cases or other similar cases, the form of (b) added to the solution may be a salt of the item listed here, such as sodium nitrite, or it may be the acid form of the item listed here, such as nitric acid. If it is the acid form, it would at least partly ionize in the polar solvent solution. That may be facilitated by adjusting the pH up where the polar solvent solution is aqueous.

The method may further comprise isolating the particles from the polar solvent solution.

The particles, whether isolated from the solution in which they are formed or not, may be dispersed in a film-forming composition to form a film-forming suspension that is the corrosion inhibitor material.

The film-forming composition may be a waterborne or organic-solvent-borne coating composition.

In specific embodiments, the film forming-composition comprises an epoxy resin or a polyurethane.

In other embodiments, the method further comprises coating the film-forming suspension on a metallic surface and curing or drying the suspension to a solid coating on the metallic surface.

Another embodiment of the invention provides a corrosion inhibitor material comprising: particles comprising: (I) a complex comprising: (a) an ionic surfactant, an ionic polymer, an ionic polymer precursor, or an ionic liquid; and (b) an ionic water-soluble corrosion inhibitor; wherein (a) and (b) have opposite charges; wherein the particles have (i) the property that if they are placed in an aqueous solution in an acidic pH they release some of the water-soluble corrosion inhibitor, (ii) the property that if they are placed in an aqueous solution in a basic pH they release some of the water-soluble corrosion inhibitor, or (iii) the property that if they are heated they release some of the water-soluble corrosion inhibitor. The particles typically further comprise (II) a solid or gel matrix structure entrapping complex (I).

In specific embodiments, the matrix structure is composed of oxides of silicon and/or oxides of one or more metals.

In specific embodiments, the particles have an average size of 50 nm to 50 microns.

In one specific embodiment, the particles further comprise polystyrene.

In specific embodiments, the material further comprises a film-forming composition in which the particles are dispersed.

In specific embodiments, the material is a solid film comprising the particles in a film matrix.

In specific embodiments, the solid film is a coating on a metal substrate.

In specific embodiments with a film-forming composition, the film-forming composition comprises an epoxy resin or a polyurethane.

EXAMPLES

Example 1—Preparation of Inorganic Controlled-Release Carriers Mo-$C_n$TA-Si (n=16) Using Cationic Surfactant Deionized (DI) water (1400 ml) and 23 g of cetyltrimethylammonium bromide ($C_{16}$TAB) surfactant were added to a 2-liter beaker. Sodium molybdate dihydrate (38.5 g) was dissolved in 400 ml DI water at room temperature and then that solution was mixed into the $C_{16}$TAB solution while agitating on a stirring hot plate at 30° C. Thereafter, 245 g of tetraethylorthosilicate (TEOS) was added to the solution and then the temperature was increased to 70° C. The reaction was promoted by agitation at 600 rpm at 70° C. for 6 hours and then the composition was aged for another 12 hours at room temperature to obtain inorganic controlled-release carriers designated herein Mo-$C_{16}$TA-Si.

After the reaction was completed, products in the reactor were separated from the bulk solution by centrifuging and washed twice with DI water, and then sieved through a 25 micron mesh. The obtained Mo-$C_{16}$TA-Si sample is dispersed back into DI water and then spray-dried in a spray dryer.

Figure 6:
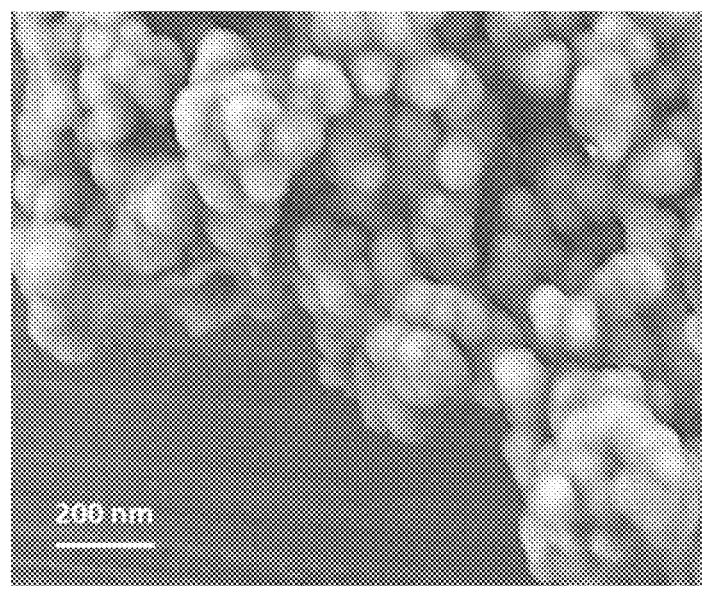
FIG. 6 shows a scanning electron microscope (SEM) micrograph of controlled-release particles of silica encapsulated sodium molybdate (Mo-$C_n$TA-Si) from Example 1.

Analysis results of a scanning electron microscope (SEM) micrograph for the prepared Mo-$C_{16}$TA-Si carriers having a spherical morphology are shown in FIG. 6. From FIG. 6, the size of the Mo-$C_{16}$TA-Si controlled-release material particles of Example 1 is 100 nm on average.

Example 2—Preparation of Inorganic Controlled-Release Carriers N—$C_n$TA-Si (n=16) Using Cationic Surfactant Potassium nitrite (70 g), and 15 g of cetyltrimethylammonium bromide ($C_{16}$TAB) were added to 1800 ml of DI water and dissolved at 30° C. Tetraethylorthosilicate (TEOS) (55 g) was added to the solution and dispersed for 30 minutes while agitating the mixture on a programmable stirring hot plate at room temperature. Thereafter, 2 g of ammonium hydroxide containing 35% ammonia by mass was diluted in 2 g of DI water to prepare an ammonium hydroxide solution, and then the ammonium hydroxide solution was added dropwise to the emulsion until the pH value was around 9. The temperature was slowly increased to 70° C. at 5° C. per minute. The reaction was continued at 70° C. for 4 hours by agitating at 300 rpm before addition of another 50 g of TEOS and 10 g of CTAB. After another 4 hours, the heat was turned off and then the reaction was completed by agitating the mixture at 500 rpm at room temperature for 12 hours to obtain inorganic controlled-release carriers named N—$C_{16}$TA-Si.

After the reaction was completed, the products in the reactor were separated by centrifuging and washed twice with DI water after sieving through a 25 micron mesh. The obtained N—$C_{16}$TA-Si sample was dispersed back into DI water and then spray dried in a spray dryer.

Figure 7:
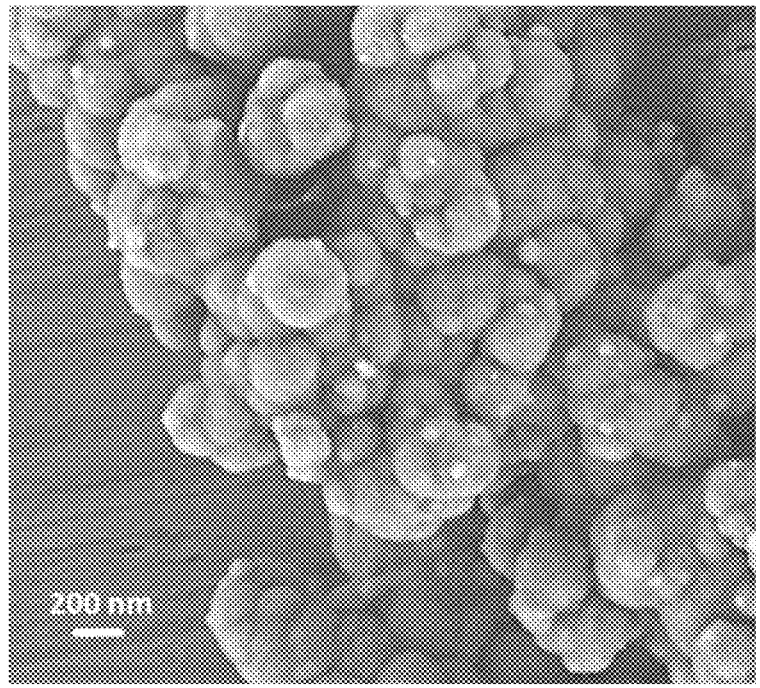
FIG. 7 shows a SEM micrograph of controlled-release particles of silica encapsulated potassium nitrite (N—$C_n$TA-Si) from Example 2.

Analysis results of a SEM micrograph for the prepared N—$C_{16}$TA-Si carriers having a spherical morphology are shown in FIG. 7. It is confirmed from FIG. 7 that the size of the N—$C_{16}$TA-Si carriers in Example 2 is 0.4 µm on average.

Example 3—Preparation of Inorganic Control-Release Initial Particles NaMBT-$C_n$TA (n=16)

CTAB (3.0 g) was completely dissolved in 125 g of DI water at 30° C. under stirring at 600 rpm. Then, 4.07 g sodium 2-mercaptobenzothiazole was added in under stirring to form a white milky suspension due to formation of NaMBT-$C_{16}$TA (refer to sodium 2-mercaptobenzothiazole-cetyltrimethylammonium) complexes. The reaction was continued for 24 hours at room temperature.

The white final product was sieved, centrifuged, washed with DI water, and air dried at room temperature and/or spray dried in a spray dryer.

Analysis results of a SEM micrograph for the prepared NaMBT-$C_{16}$TA initial particles with irregular morphology are shown in FIG. 8. It is confirmed from FIG. 8 (on the left hand side) that the size of the NaMBT-$C_{16}$TA (refer to sodium 2-mercaptobenzothiazole-cyltrimethylammonium) carriers in example 3 is 3 µm on average. It is shown in FIG. 8 (on the right hand side) that the inhibitor 2-mercaptobenzothiazole (black area) released from the melted initial particles (white crystals of $C_{16}$TA in the right panel) after heating.

Example 4—Preparation of Inorganic Controlled-Release Carriers NaMBT-$C_n$TA-Si (n=16)

CTAB (3.0 g) was completely dissolved in 125 g of DI water at 30° C. under stirring at 600 rpm. Then, 4.07 g sodium 2-mercaptobenzothiazole was added while stirring to form a white milky suspension due to formation of NaMBT-$C_{16}$TA (refer to sodium 2-mercaptobenzothiazole-cyltrimethylammonium) complexes. The heat was turned off, and the reaction was continued for 24 hours at room temperature. Tetramethyl orthosilicate (TMOS) (10.0 g) was added while stirring at room temperature. After further stirring for 3 hours, 100 g of DI water was added. And then, the reaction was continued for another 24 hours at room temperature.

The white final product was sieved, centrifuged, washed with DI water, and air dried at room temperature and/or spray dried in a spray dryer.

Figure 9:
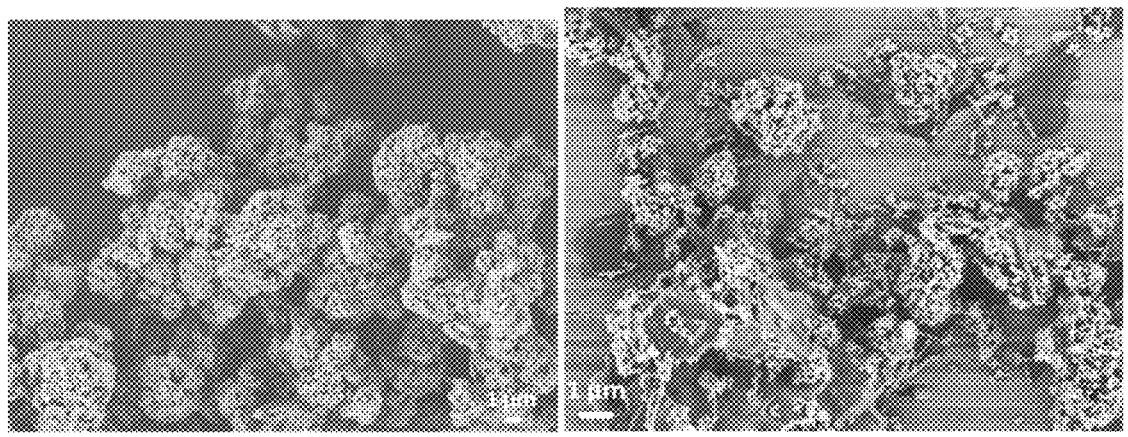
FIG. 9 shows SEM micrographs of the controlled-release material NaMBT-$C_n$TA-Si from Example 4 before heating (image on left side) and after heating (image on right side).

Analysis results of a scanning electron microscopy (SEM) image of the prepared NaMBT-$C_{16}$TA-Si particles with irregular morphology are shown in FIG. 9. It is confirmed from FIG. 9 (on the left hand side) that the size of the NaMBT-$C_n$TA-Si carriers in Example 4 is 5 µm on average. The particles were heated, and it is shown in FIG. 9 (on the right hand side) that the inhibitor 2-mercaptobenzothiazole escaped from the porous particles on heating.

Example 5—Preparation of Inorganic Controlled-Release Carriers MBT-$C_n$TA-Si (n=16)

Cetyltrimethylammonium bromide ($C_{16}$TAB) (23 g) was added to 1400 ml DI water in a beaker while stirring at room temperature. Then, 38.5 g of 2-mercaptobenzothiazole (MBT) was mixed into the solution. In 1 hour, 110 g of tetraethylorthosilicate (TEOS) was added while stirring at 600 rpm. Then 2 g of ammonium hydroxide containing 17.5% ammonia by mass was diluted in 2 g of DI water to prepare ammonium hydroxide solution, and then the ammonium hydroxide solution was added dropwise to the emulsion solution until the pH value was around 9. The reaction was continued at 70° C. for 12 hours by agitating it at 500 rpm before the heat was turned off. Then, the reaction was completed by agitating the mixture at 500 rpm at room temperature for another 12 hours to obtain inorganic controlled-release carriers named MBT-$C_{16}$TA-Si.

After the reaction was completed, the product was separated by centrifuging and washed twice with DI water and then sieved through a 25 micron mesh. The obtained MBT-$C_{16}$TA-Si sample was dispersed back into DI water and then spray-dried in a spray dryer.

Figure 10:
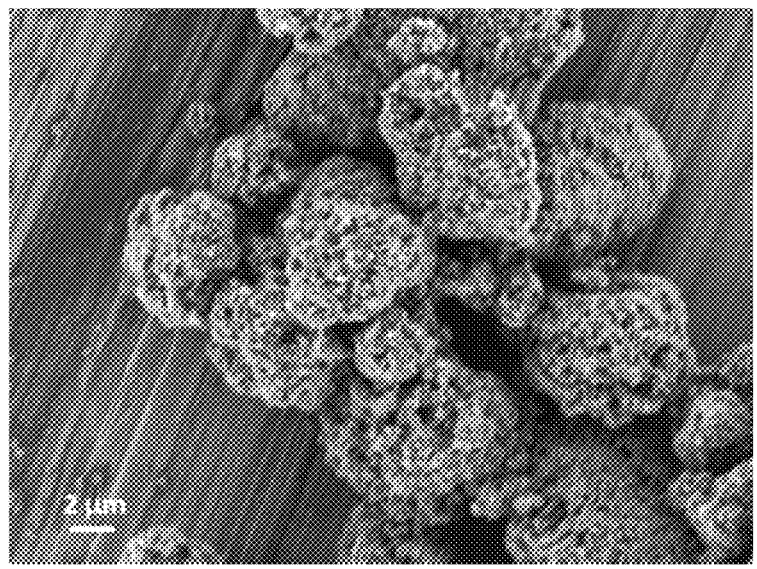
FIG. 10 shows a SEM micrograph of silica-encapsulated potassium nitrite (MBT-$C_n$TA-Si) from Example 5.

Analysis results of a SEM micrograph for the prepared MBT-$C_{16}$TA-Si carriers having a spherical morphology are shown in FIG. 10. It is confirmed from FIG. 10 that the size of the MBT-$C_{16}$TA-Si carriers in Example 5 is 6 μm on average.

Example 6—Preparation of Inorganic Controlled-Release Carriers Mo-AMC-Si Using Ionic Liquid The ionic liquid 1-alkyl-3-methylimidazolium chloride (AMC) (2.5 g) was added to 200 ml of DI water. Sodium molybdate dihydrate (5.5 g) was dissolved in 200 ml DI water at room temperature and then the molybdate solution was mixed into the AMC solution while agitating on a stirring hot plate. Thereafter, 34 g of tetraethylorthosilicate (TEOS) was added to the solution and the solution heated to 80° C. The reaction was performed by agitation at 500 rpm at 80° C. for 6 hours and then was continued at room temperature for another 12 hours. This produced inorganic controlled-release carriers named Mo-AMC-Si.

After the reaction, the product was separated by centrifuging and washed twice using DI water. The obtained Mo-AMC-Si sample was dispersed back into DI water and sieved through a 25 micron mesh then air dried in the hood.

Example 7—Preparation of Inorganic Controlled-Release Carriers Mo-βCD-Si Using Supramolecule β (beta)-cyclodextrin (β-CD) (3.5 g) was dissolved in 200 ml DI water. Sodium molybdate dihydrate (5.5 g) was dissolved in 200 ml DI water at room temperature and then the sodium molybdate solution was added into the β-CD solution while agitating on a stirring hot plate. Thereafter, 34 g of tetraethylorthosilicate (TEOS) was added in the solution and the solution heated to 70° C. The reaction was performed by agitation at 500 rpm at 70° C. for 6 hours, and then continued at room temperature for another 12 hours to obtain inorganic controlled-release carriers named Mo-βCD-Si.

After the reaction completed, product was separated by centrifuging and washed twice using DI water. The obtained Mo-βCD-Si sample was dispersed back into DI water and sieved through a 25 micron mesh then air dried in the hood.

Example 8—Preparation of Inorganic Controlled-Release Carriers Mo-MPTA-Si Using Block Polymer 3.0 g of 3-(methacryloylamino) propyl trimethylammonium chloride (MPTA) (a polymerizable monomer) was added to 200 ml DI water. Sodium molybdate dihydrate (5.5 g) was dissolved in 200 ml DI water at room temperature, and then that solution was mixed into the MPTA solution while agitating on a stirring hot plate. Thereafter, 34 g of tetraethylorthosilicate (TEOS) was added to the solution and the solution heated to 80° C. The reaction was continued with agitation at 500 rpm at 80° C. for 6 hours, and then continued for another 12 hours at room temperature to obtain inorganic controlled-release carriers named Mo-MPTA-Si.

After the reaction completed, product was separated by centrifuging and washed twice using DI water. The obtained Mo-MPTA-Si sample was dispersed back into DI water and sieved through a 25 micron mesh then air dried in the hood.

Example 9—Preparation of Inorganic Control-Release Carriers Mo-$C_n$TA-SiAl (n=16)

Cetyltrimethylammonium bromide ($C_{16}$TAB) (23 g) was added to 1400 ml DI water and dissolved at 30° C. Sodium molybdate dihydrate (38.5 g) was dissolved in 400 ml DI water at room temperature, and that solution was then added to the $C_{16}$TAB solution while agitating on a stirring hot plate. Then, 24 g aluminum chloride and 221 g of tetraethylorthosilicate (TEOS) was put in the solution and the solution heated to 70° C. The reaction was continued by agitation at 500 rpm at 70° C. for 6 hours and then was continued for another 24 hours at room temperature to obtain inorganic controlled-release carriers named Mo-$C_{16}$TA-SiAl.

After the reaction completed, product was separated by filtering and washed twice using DI water. The obtained Mo-$C_{16}$TA-SiAl sample was dispersed back into DI water and sieved through a 25 micron mesh then spray-dried in a spray dryer.

Example 10—Preparation of Inorganic Control-Release Carriers N—$C_n$TA-SiTi (n=16)

Potassium nitrite (70 g) and 15 g of cetyltrimethylammonium bromide ($C_{16}$TAB) were dissolved at 30° C. in 1800 ml of DI water. Tetraethylorthosilicate (TEOS) (55 g) was then added and dispersed for 30 minutes while agitating the mixture on a programmable stirring hot plate at room temperature. Thereafter, 2 g of ammonium hydroxide containing 35% ammonia by mass was diluted in 2 g of DI water to prepare ammonium hydroxide solution, and then the ammonium hydroxide solution was added dropwise to the reaction mixture until the pH value was around 9. The temperature was slowly increased to 70° C. by 5° C. per minute. The reaction was continued at 70° C. for 4 hours with agitation at 300 rpm before addition of 50 g of titanium (IV) butoxide and 10 g of CTAB. After another 4 hours, the heat was turned off then the reaction was continued with agitation at 500 rpm at room temperature for 12 hours to obtain inorganic controlled-release carriers named N—$C_{16}$TA-SiTi.

After the reaction completed, product in the reactor was separated by centrifuging and washed twice using DI water. The obtained N—$C_{16}$TA-SiTi sample was dispersed back into DI water and sieved through a 25 micron mesh then spray-dried in a spray dryer.

Example 11—Preparing of Controlled Release of Inorganic Carriers MBT-$C_n$TA-SiPS (n=16)

Polystyrene monohydroxyl terminated MW 10 000 (PS 10,000) (0.5 g) was dissolved in 3.0 mL of toluene and 50 mL ethanol. Then 2.0 mL dimethyloctadecyl[3-(trimethoxysilyl)propyl]ammonium chloride was added to the toluene solution. In a 125-mL flask, 1.6 g 2-mercaptobenzothiazole (MBT) was dissolved in 5 g of Triton X-100 to obtain a clear yellow solution. Then the polystyrene solution was mixed with the MBT solution, and then, 2 g of ammonium hydroxide solution containing 17.5% ammonia by mass was dropped in the solution until the pH value was around 10 (as an alternative to adding 1.6 g of MBT and then adding ammonium hydroxide solution, 1.6 g of ammonium mercaptobenzothiazole dissolved in DI water could be added).

After stirring for 24 hours, the reaction was completed. The product was separated by centrifuging and washed twice using DI water. The obtained MBT-$C_{16}$TA-SiPS sample was dispersed back into DI water and sieved through a 25 micron mesh then spray-dried in a spray dryer.

Example 12—Preparation of Epoxy Coating with Controlled-Release Particles

Controlled-release particles (0.5 g) were mixed with 7.3 g solvent methyl isobutyl ketone and the mixture was sonicated for 2 minutes. Dow D. E. R. 671-X75 epoxy resin (10.6 g) was then added and the mixture was blended at 600 rpm for 40 minutes using a propeller mixer. Dow PAPI 27 polymeric isocyanate hardener (2.0 g) was added and mixed at 600 rpm for 20 minutes followed by sonication for 5 minutes. The coating was applied to an acetone-cleaned phosphatized carbon steel panel using a wire draw bar giving approximately 3.6 mils of wet film thickness. The coated panel was immediately put into an enclosed cabinet for 1 hour then allowed to air dry. After air drying for 24 hours, the coated panel was placed into a 170° C. oven for 20 minutes. Tape was applied to uncoated back and edges of coated panels then the coated panels were scribed with a single center-aligned vertical scribe using a generic scribing tool.

Example 13—Preparation of Waterborne Coating with Controlled-Release Particles

Controlled-release particles (0.5 g) were mixed with 0.56 ml DI water, and the mixture was sonicated for 2 minutes. Waterborne acrylic coating (10.6 g) was then added to the wetted particles and the suspension was mixed by hand for 10 minutes or until coating was thoroughly mixed. The obtained coating was applied to an acetone-cleaned carbon steel panel using a wire draw bar giving approximately 8 mils of wet film thickness. The coated panel was air dried for 24 hours. After drying, a second coat of the same coating with no particles was applied and air dried and then cured for 30 days in the air. Tape was applied to uncoated back and edges of coated panels then the coated panels were scribed with a single center-aligned vertical scribe using a generic scribing tool.

Example 14—Corrosion Protection Test

Figure 11:
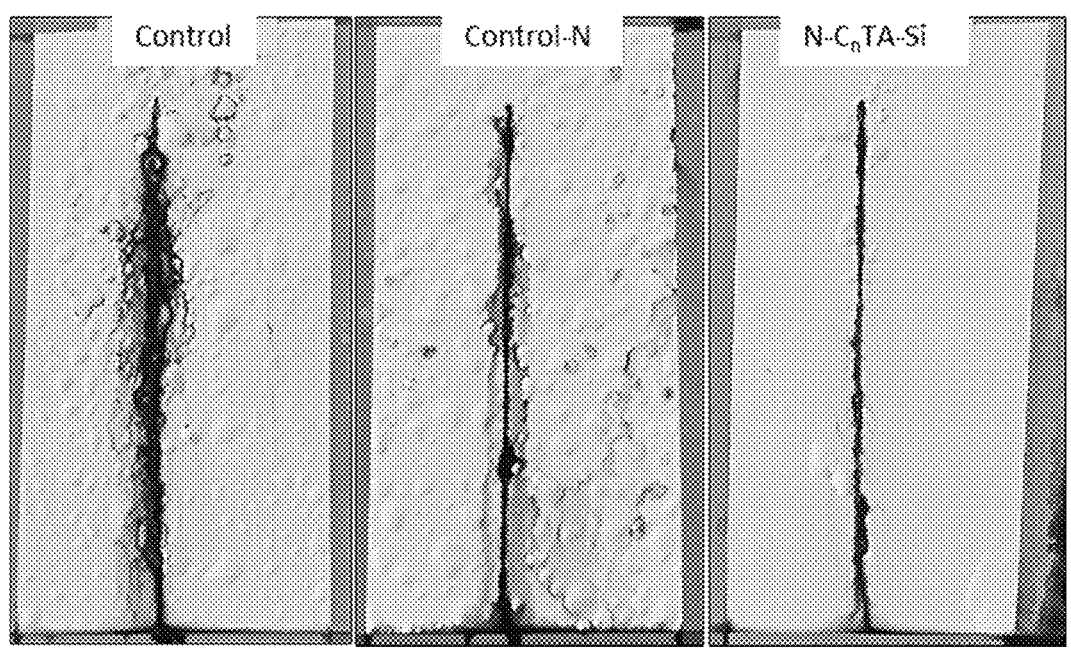
FIG. 11 shows the results of 789 hours of salt fog testing of a waterborne coating embedded with inorganic controlled-release device of silica encapsulated potassium nitrite (N—$C_n$TA-Si).

N—$C_n$TA-Si particles prepared in accordance with Example 2 were dispersed into a waterborne coating as in Example 12 that was applied to steel panels as in Example 12. The waterborne coating material was tested for corrosion protection after being applied on a carbon steel panel, scribed and placed in a salt fog chamber for 789 hours for salt fog testing. Control panels with coating with no particles added (Control) and with coating that has pure potassium nitrite mixed (Control-N) were also tested for comparison. The results are shown in FIG. 11. Compared to a control coating in which no any inhibitor was incorporated and a coating with pure potassium nitrite mixed in, the coating with N—$C_n$TA-Si device embedded demonstrated better protection for the metal substrate from corrosion in the corrosive environment of the salt fog chamber.

Example 15—Release of Active Agent in Basic Solution

In this Example, the release of the active agent from materials of the invention is tested in 0.1 M potassium hydroxide solution.

Figure 3:
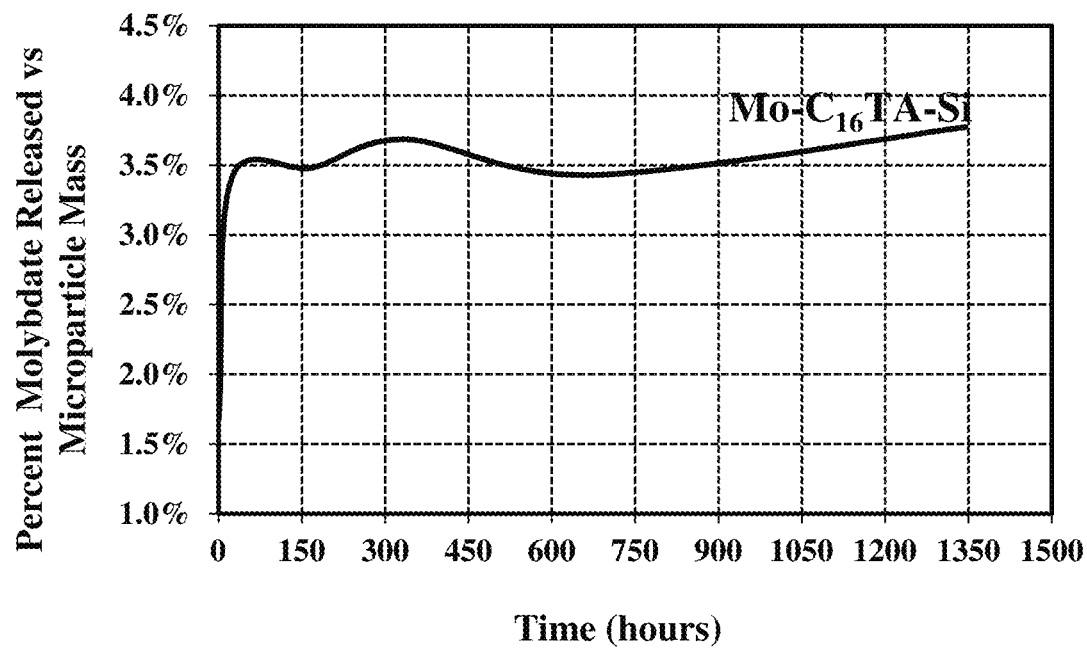
FIG. 3 is a graph of release data of molybdate from silica-encapsulated sodium molybdate (Mo-$C_n$TA-Si).
Figure 4:
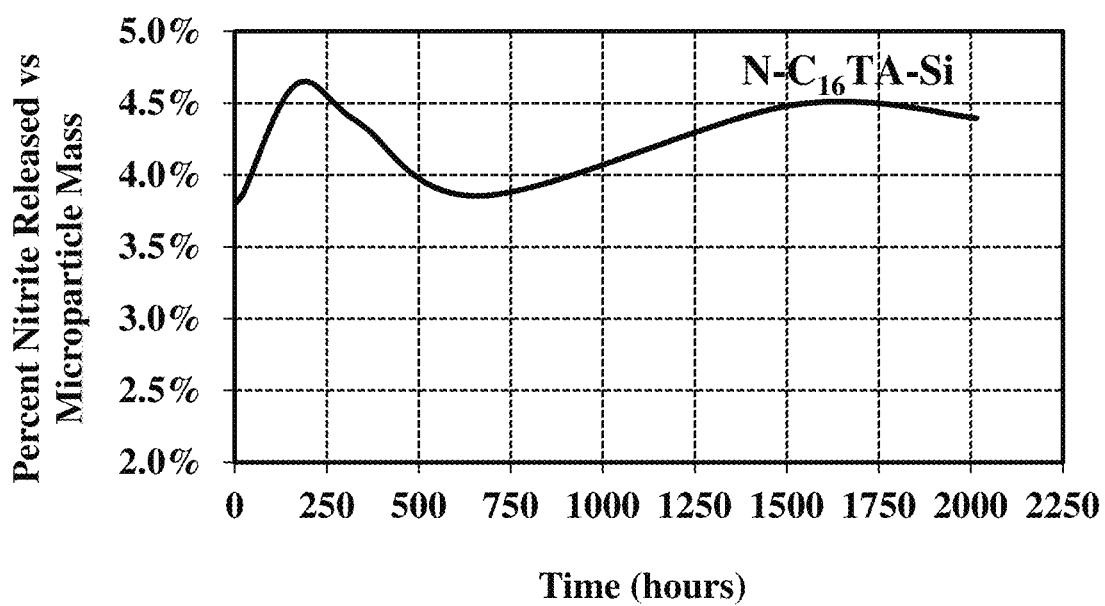
FIG. 4 is a graph of release data of nitrite from silica-encapsulated potassium nitrite (N—$C_n$TA-Si).
Figure 5:
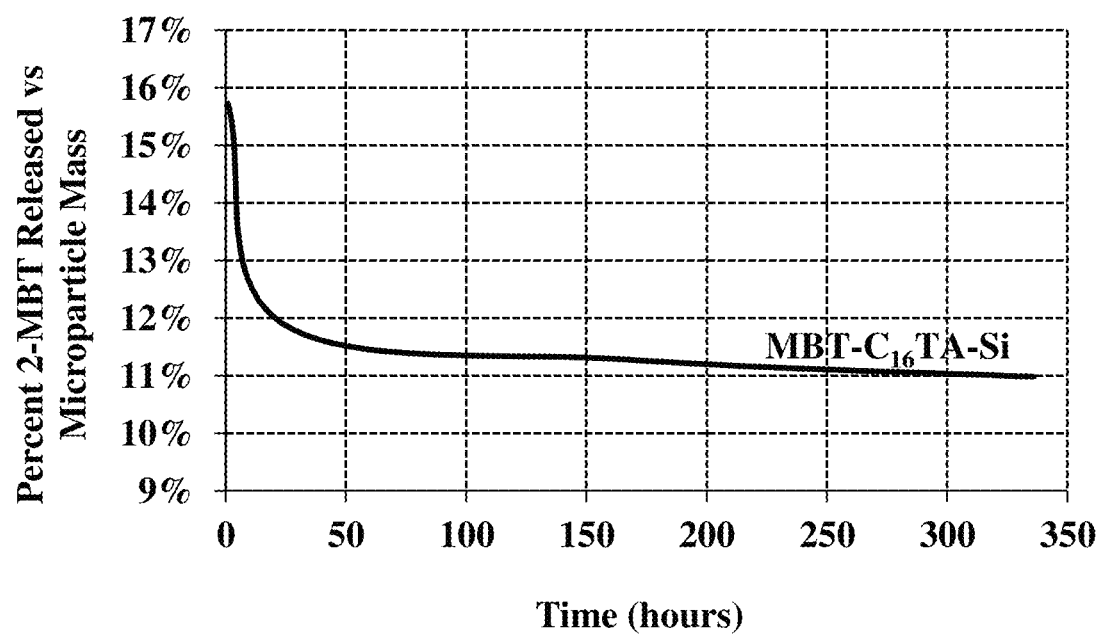
FIG. 5 is a graph of release data of mercaptobenzothiazole from silica-encapsulated sodium mercaptobenzothiazole (MBT-$C_n$TA-Si).

In FIGS. 3-5, release plots for inorganic controlled-release materials in a 0.1 M potassium hydroxide (KOH) solution is shown. The ordinate axis shows the time in hours while the abscissa axis shows the percentage of the inhibitor by weight of the added controlled-release material that is found in the bulk KOH solution.

FIG. 3 shows release of molybdate from Mo-$C_{16}$TA-Si (made in Example 1) controlled-release material in 0.1 M KOH.

The N—$C_{16}$TA-Si controlled-release material (Example 10) was tested. The result for release of the nitrite active agent is shown in FIG. 4.

FIG. 5 shows release of MBT from MBT-$C_{16}$TA-Si (made in Example 5) controlled-release material in 0.1 M KOH.

These data demonstrate both immediate and prolonged response to alkaline pH. The data also indicate that released active agent can be taken up again by the cationic surfactant or the silica matrix of the corrosion inhibitor. However, it should be noted that the released active compounds in the bulk solution are not consumed by anticorrosive reactions at they should be in the corrosive environment on a metallic substrate.

Although the present invention has been disclosed in terms of a number of preferred embodiments, it will be understood that numerous modifications and variations could be made thereto without departing from the scope of the invention as defined by the following claims.

All cited references are incorporated by reference in their entirety.

We claim:

1. A corrosion inhibitor material comprising:
   particles comprising:
      (I) a complex comprising:
         (a) an ionic surfactant, an ionic polymer, an ionic polymer precursor, or an ionic liquid; and
         (b) an ionic water-soluble corrosion inhibitor;
      wherein (a) and (b) have opposite charges and (a) and (b) are bonded to one another;
      wherein the particles are embedded in the framework of: a solid or gel matrix structure;
      wherein the particles have (i) the property that if they are placed in an aqueous solution in an acidic pH they release some of the water-soluble corrosion inhibitor, (ii) the property that if they are placed in an aqueous solution in a basic pH they release some of the water-soluble corrosion inhibitor, or (iii) the property that if they are heated they release some of the water-soluble corrosion inhibitor.

2. The material of claim 1 wherein the matrix structure is composed of oxides of silicon, oxides of one or more metals, or combinations thereof.

3. The material of claim 2 wherein the particles further comprise polystyrene.

4. The material of claim 1 wherein the particles have an average size of 50 nm to 50 microns.

5. The material of claim 1 further comprising a liquid film-forming composition in which the particles are dispersed.

6. The material of claim 5 wherein the film-forming composition comprises an epoxy resin, or is a polyurethane.

7. The material of claim 1 wherein the material is a solid film comprising the particles in a film matrix.

8. The material of claim 7 wherein the solid film is a coating on a metal substrate.

9. The material of claim 1 wherein breaking the bond between (a) and (b) releases the ionic water-soluble corrosion inhibitor.

10. A corrosion inhibitor material comprising:
particles comprising:
(I) a complex comprising:
(a) cyclodextrin and (b) an ionic water-soluble corrosion inhibitor, bonded to (a);
wherein particles are embedded in the framework of a solid or gel matrix structure;
wherein the matrix structure is composed of oxides of silicon, oxides of one or more metals, or combinations thereof;
wherein the particles have (i) the property that if they are placed in an aqueous solution in an acidic pH they release some of the water-soluble corrosion inhibitor, (ii) the property that if they are placed in an aqueous solution in a basic pH they release some of the water-soluble corrosion inhibitor, or (iii) the property that if they are heated they release some of the water-soluble corrosion inhibitor.

11. The material of claim 10 wherein breaking the bond between (a) and (b) releases the ionic water-soluble corrosion inhibitor.

\* \* \* \* \*